US012806243B2

(12) United States Patent
Sarasa Barrio

(10) Patent No.: US 12,806,243 B2
(45) Date of Patent: Nov. 24, 2026

(54) AMYLOID CONJUGATE AND USES AND METHODS THEREOF

(71) Applicant: ARACLON BIOTECH, S.L., Saragossa (ES)

(72) Inventor: Manuel Sarasa Barrio, Saragossa (ES)

(73) Assignee: ARACLON BIOTECH, S.L., Saragossa (ES)

( * ) Notice: Subject to any disclaimer, the term of this patent is extended or adjusted under 35 U.S.C. 154(b) by 1237 days.

(21) Appl. No.: 17/679,723

(22) Filed: Feb. 24, 2022

(65) Prior Publication Data

US 2022/0184178 A1 Jun. 16, 2022

Related U.S. Application Data

(63) Continuation of application No. 16/855,263, filed on Apr. 22, 2020, now abandoned, which is a continuation of application No. 16/103,810, filed on Aug. 14, 2018, now abandoned, which is a continuation of application No. PCT/EP2017/053242, filed on Feb. 14, 2017.

(30) Foreign Application Priority Data

Feb. 15, 2016 (ES) ................................ ES201630173

(51) Int. Cl.

| | |
|---|---|
| ***A61K 38/17*** | (2006.01) |
| ***A61K 9/06*** | (2006.01) |
| ***A61K 38/03*** | (2006.01) |
| ***A61K 39/39*** | (2006.01) |
| ***A61K 47/42*** | (2017.01) |
| ***A61K 47/64*** | (2017.01) |
| ***A61P 25/28*** | (2006.01) |
| ***C01F 7/02*** | (2022.01) |
| ***C07K 7/06*** | (2006.01) |
| ***C07K 14/435*** | (2006.01) |
| ***C07K 14/47*** | (2006.01) |
| ***C07K 16/18*** | (2006.01) |
| *A61K 39/00* | (2006.01) |

(52) U.S. Cl.

CPC ............ *A61K 38/1767* (2013.01); *A61K 9/06* (2013.01); *A61K 38/03* (2013.01); *A61K 39/39* (2013.01); *A61K 47/42* (2013.01); *A61K 47/643* (2017.08); *A61K 47/646* (2017.08); *A61P 25/28* (2018.01); *C01F 7/02* (2013.01); *C07K 7/06* (2013.01); *C07K 14/43504* (2013.01); *C07K 14/4711* (2013.01); *C07K 16/18* (2013.01); *A61K 2039/55505* (2013.01); *C07K 2317/33* (2013.01); *C07K 2319/00* (2013.01); *C07K 2319/31* (2013.01)

(58) Field of Classification Search

CPC ........ A61K 38/03; A61K 38/04; A61K 38/08; A61K 38/1767; A61K 39/39; A61K 47/643; A61K 47/646; A61K 47/42; A61K 2039/55505; C07K 7/06; C07K 14/43504; C07K 14/4711; C07K 16/18; C07K 2317/33; C07K 2319/00; C07K 2319/31; C01F 7/02

See application file for complete search history.

(56) References Cited

U.S. PATENT DOCUMENTS

| | | | | |
|---|---|---|---|---|
| 4,666,829 | A | 5/1987 | Glenner | |
| 2007/0154480 | A1 | 7/2007 | Schenk | |
| 2009/0098155 | A1 | 4/2009 | Garsky et al. | |
| 2009/0162361 | A1 | 6/2009 | Nakamura | |
| 2009/0162362 | A1 * | 6/2009 | Sarasa Barrio | C07K 7/06 424/139.1 |
| 2010/0068214 | A1 | 3/2010 | Rood | |
| 2011/0268756 | A1 | 11/2011 | Matsuda | |
| 2012/0244159 | A1 | 9/2012 | Chain | |
| 2013/0011431 | A1 * | 1/2013 | Ulrich | A61K 39/385 424/196.11 |
| 2013/0022630 | A1 | 1/2013 | Wisniewski | |
| 2013/0164217 | A1 | 6/2013 | Umek et al. | |
| 2013/0230545 | A1 | 9/2013 | Markus et al. | |
| 2020/0140488 | A1 | 5/2020 | Barrio | |

FOREIGN PATENT DOCUMENTS

| | | | |
|---|---|---|---|
| ES | 2246105 | B1 | 3/2007 |
| RU | 2385161 | C2 | 3/2010 |
| RU | 2526155 | C2 | 8/2014 |
| RU | 2533806 | C2 | 11/2014 |
| RU | 2603486 | C2 | 11/2016 |
| WO | WO 99/27944 | A1 | 6/1999 |
| WO | WO 00/72880 | A2 | 12/2000 |
| WO | WO 2004/067561 | A1 | 8/2004 |
| WO | WO 2005/058940 | A2 | 6/2005 |
| WO | WO 2005/058941 | A2 | 6/2005 |
| WO | WO 2005/072777 | A2 | 8/2005 |
| WO | WO 2005/123775 | A1 | 12/2005 |
| WO | WO 2006/094724 | A2 | 9/2006 |
| WO | WO 2007/062852 | A2 | 6/2007 |

(Continued)

OTHER PUBLICATIONS

ChemTrade product profile sheet for Rehydragel® adjuvants, 2 pages, revision date: Sep. 23, 2015. (Year: 2015).*

(Continued)

*Primary Examiner* — Kimberly Ballard
(74) *Attorney, Agent, or Firm* — Knobbe, Martens, Olson & Bear

(57) ABSTRACT

A composition includes aluminum hydroxide gel and a conjugate of at least one CysA13(33-40) peptide linked to the keyhole limpet hemocyanin (KLH). Maleimidobutyric acid Nhydroxysuccinimide ester (SM) serves as cross-linking agent. The composition can produce an effective and specific immune response against Aβ40. The antibodies produced are specific for Aβ40 without significantly binding to Aβ42. The composition can increase the response against Aβ40 compared with the response produced by other conjugates that include CysAβ(33-40) peptide and KLH, and are bound or conjugated by other crosslinking agents.

9 Claims, No Drawings

Specification includes a Sequence Listing.

(56) References Cited

FOREIGN PATENT DOCUMENTS

| | | | | |
|---|---|---|---|---|
| WO | WO 2007/064917 A2 | | 6/2007 | |
| WO | WO 2007/096076 A2 | | 8/2007 | |
| WO | WO 2009/056490 A1 | | 5/2009 | |
| WO | WO 2009/090650 A2 | | 7/2009 | |
| WO | WO 2010/010469 A2 | | 1/2010 | |
| WO | WO 2010/011947 A2 | | 1/2010 | |
| WO | WO 2010/044464 A1 | | 4/2010 | |
| WO | WO 2010/087771 A1 | | 8/2010 | |
| WO | WO-2010136487 A1 | * | 12/2010 | .............. A61P 43/00 |
| WO | WO 2011/120924 A1 | | 10/2011 | |
| WO | WO 2012/073111 A2 | | 6/2012 | |
| WO | WO 2015/128287 A1 | | 9/2015 | |

OTHER PUBLICATIONS

CovaChem product sheet for GMBS Crosslinker, retrieved Mar. 26, 2026 from www.covachem.com/gmbs-maleimidobutyric-acid-N-succinimidyl-ester-80307-12-6.html. (Year: 2026).*

Kafi K et al. Maleimide conjugation markedly enhances the immunogenicity of both human and murine idiotype-KLH vaccines. Mol. Immunol. 2009, 46:448-456. (Year: 2009).*

Ida N et al. Analysis of heterogeneous A4 peptides in human cerebrospinal fluid and blood by a newly developed sensitive Western blot assay. J. Biol Chem. 1996, 271(37):22908-22914. (Year: 1996).*

CovaChem webpage for GMBS Crosslinker, retrieved Feb. 19, 2019 from www.covachem.com/gmbs-maleimidobutyric-acid-N-succinimidyl-ester-80307-12-6.html. (Year: 2019).

Examination Report on Patentability, dated Aug. 14, 2019, for Colombian Application No. NC2018/0007557.

International Search Report, mailed Dec. 4, 2017, in International Application No. PCT/EP2017/053242.

Kafi, K., et al., Maleimide conjugation markedly enhances the immunogenicity of both human and murine idiotype-KLH vaccines, Molecular Immunology, vol. 46, No. 3, pp. 448-456, 2009.

Krejci, J., et al., Effects of adjuvants on the immune response of pigs after intradermal administration of antigen, Research in Veterinary Science, vol. 94, No. 1, pp. 73-76, 2013.

Maleimide Activated BSA, KLH Conjugation Kit, Sigma-Aldrich, Catalog No. MBK1, 6 pages. (Year: 2012).

Office Action for Russian Application No. 2018126395/04(041818) dated Jul. 5, 2019.

Search Report for Russian Application No. 2018126395/04(041818) dated Jul. 5, 2019.

Yixian, G., et al., Potent antigen-specific immune response induced by infusion of spleen cells coupled with succinimidyl-4-(N-maleimidomethyl cyclohexane)-1-carboxylate (SMCC) conjugated antigens, International Immunopharmacology, vol. 31, pp. 158-168, 2015.

Yaguchi, Y, et al., Anti-Amyloid B-Protein Antibody, The Cell, vol. 33, No. 2, pp. 20-21, 2001.

Office Action dated Mar. 7, 2021 received in Israeli Application No. 201630173 in 4 pages.

Search Report dated May 12, 2016 in Spanish Application No. ES 201630173.

* cited by examiner

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial sequence
<220> FEATURE:
<223> OTHER INFORMATION: Abeta fragment with cysteine added at the
      N-terminus

<400> SEQUENCE: 1

Cys Gly Leu Met Val Gly Gly Val Val
1               5


<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40


<210> SEQ ID NO 3
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

AMYLOID CONJUGATE AND USES AND METHODS THEREOF

PRIORITY AND CROSS REFERENCE TO RELATED APPLICATIONS

This application is a Continuation Application of U.S. application Ser. No. 16/855,263, filed Apr. 22, 2020, which is a Continuation Application of U.S. application Ser. No. 16/103,810, filed Aug. 14, 2018, which is a Continuation Application of International Application No. PCT/EP2017/053242, filed Feb. 14, 2017, designating the U.S. and published in English as WO 2017/140656 A1 on Aug. 24, 2017, which claims the benefit of Spanish Patent Application No. ES201630173, filed Feb. 15, 2016. All applications for which a foreign or a domestic priority is claimed are identified in the Application Data Sheet filed herewith and are hereby incorporated by reference in their entirety under 37 C.F.R. § 1.57.

REFERENCE TO ELECTRONIC SEQUENCE LISTING

The present application includes an Electronic Sequence Listing. The Electronic Sequence Listing is provided as a file entitled DURC059001C2SEQLIST.txt, which is 1,304 bytes in size, created and last modified on Feb. 19, 2022. The information in the Electronic Sequence Listing is incorporated herein by reference in its entirety.

Field

The present invention relates to the field of biochemistry, more specifically to the field of sector of protein conjugation. Additionally, the present invention has an application in the field of medicine and veterinary science in the treatment of amyloid diseases.

Background

Multiple conjugates useful for the active or passive immunization of patients with amyloid diseases, fundamentally for Alzheimer's disease, have been described in the prior art. It should be pointed out that most of said prior art focuses on selecting peptides or transport proteins that allow generating a suitable immune response in patients, the crosslinking agent used not being given much importance or relevance. Said crosslinking agent is often expressed in the form of a list of all those that are available or known up until now indicating that any of them can be used in an equivalent manner, or it is simply not even indicated.

For example, Spanish patent application with publication number ES2246105 discloses the prevention or treatment of amyloid diseases, inter alia Alzheimer's disease, by means of the active immunization of patients with the conjugate formed by the Aβ33-40 peptide and the transport protein keyhole limpet hemocyanin (hereinafter, KLH), with accession number 4BED in the Protein Data Bank. The use of said conjugate for generating antibodies (for example, by means of immunizing mammals or birds with said conjugate) which are subsequently used in a passive immunization method for the prevention or treatment of amyloid diseases, inter alia Alzheimer's disease, is also contemplated. Said patent document does not specify the crosslinking agent used.

The only prior art document of which the inventors are aware and in which the crosslinking agent is considered important in the immune response produced in the conjugate is PCT patent application with publication No. WO2005/072777. Said document discloses conjugates for the active or passive immunization of patients based on the crosslinking agent LPA with respect to which the capacity thereof for binding with or having two peptides at the same time is highlighted, making it appropriate for generating an immune response suitable in patients. Within the general explanation of an LPA-based conjugate it is contemplated that the peptide used may be an Aβ42 or Aβ40 C-terminal fragment, and fragments 33-42, 35-42, 36-42, 37-42, 38-42 and 39-42 are specifically mentioned and exemplified. Additionally, said document mentions that the transport protein may be KLH. This same document describes generating other conjugates, using a different crosslinking agent (N-succinimidyl 3-(2-pyridyldithio) propionate, commonly known as SPDP).

SUMMARY

After extensive and thorough experimentation, the inventors have surprisingly discovered that maleimidobutyric acid N-hydroxysuccinimide ester (hereinafter, SM), a heterobifunctional crosslinking agent, in which each molecule thereof binds a peptide to the transport protein, used as a crosslinking agent for preparing CysAβ3(33-40) peptide (SEQ ID NO: 1) and KLH conjugates, produces conjugates that allow generating an improved immune response in comparison to the immune response produced by conjugates generated with other homo- or heterobifunctional crosslinking agents of the prior art such as SPDP which also allow the binding of a peptide to the transport protein. Such improvement is clearly shown in examples 1 to 4 of the present specification. In addition, said examples show that said new conjugates or the pharmaceutical compositions comprising said conjugates produce:

- an immune response that is as specific as possible, for the purpose of minimizing the side effects associated with the (preventive or therapeutic) vaccine treatment;
- the highest possible immune response for the purpose of assuring an effective immunization of patients and reducing the required doses of immunogenic conjugate.

Thus in a first aspect, the present invention relates to a conjugate characterized in that the crosslinking agent is SM.

In another aspect, the present invention relates to a composition comprising the conjugate of the present invention.

In additional aspects of the present invention, the use of said conjugate for preparing a medicinal product, more specifically, a medicinal product intended for the treatment or prevention of amyloid diseases, is contemplated.

Another aspect to which the present invention relates is to compositions comprising the conjugate of the present invention for use as a medicinal product, more specifically for use in the treatment or prevention of amyloid diseases.

Additionally, the present invention also relates to a method of treatment or prevention of an amyloid disease by means of the delivery of a composition comprising the conjugate of the present invention.

In yet another aspect, the present invention relates to a method of manufacturing antibodies based on the use of the conjugate of the present invention.

DETAILED DESCRIPTION

Definitions

As used herein, "amyloid disease" and the plural thereof refer to diseases associated with the β-amyloid accumulation. Said accumulation can fundamentally occur in the brain, producing diseases among which are found Alzheimer's disease, Parkinson's disease, cerebral amyloid angiopathy, vascular dementia of an amyloid origin and dementia with Lewy bodies. β-amyloid accumulation can also fundamentally occur in skeletal muscle, producing inclusion-body myositis.

As used herein, "passive immunization" and the plural thereof refer to the delivery of antibodies or fragments thereof to a patient with the intention of conferring immunity to said patient.

As used herein, "active immunization" and the plural thereof refer to the delivery to a patient of peptides (in the form of conjugates) acting as immunogens, i.e., they allow antibody generation with the intention of conferring immunity to said patient.

As used herein, "adjuvant" and the plural thereof refer to immunomodulatory substances capable of being combined with the conjugate of the present invention for increasing, improving or otherwise modulating an immune response in a patient.

As used herein, "patient" and the plural thereof refer to any mammal, preferably human, in which the conjugate of the present invention or a composition comprising same can be administered for the purpose of treating, preventing or delaying onset of an amyloid disease.

As used herein, "CysAβ(33-40)" refers to the sequence of positions 33 to 40 of Aβ40 (SEQ ID NO: 2) to which a cysteine has been added at the N-terminus. Said sequence is reflected in SEQ ID NO: 1 and is: CGLMVGGVV.

Description

A first aspect the present invention relates to a conjugate comprising at least one CysAβ(33-40) peptide (SEQ ID NO: 1) and keyhole limpet hemocyanin (KLH), characterized in that the crosslinking agent connecting each of the components of the conjugate (each of said at least one peptide with KLH) is maleimidobutyric acid N-hydroxysuccinimide ester (SM).

Said conjugate, in addition to allowing or producing an effective and specific immune response against Aβ40 (the antibodies produced are specific for Aβ40 without significantly binding to Aβ42), increases said response compared with the response produced by other conjugates also comprising CysAβ(33-40) peptide (SEQ ID NO: 1) and KLH, and in which said elements have been bound or conjugated by means of another crosslinking agent that also allow the binding of a peptide to the transport protein. In a second aspect, the present invention relates to a composition comprising the conjugate of the present invention.

In a preferred embodiment, the composition additionally comprises one or more adjuvants, which are preferably selected from mineral salts (such as aluminum hydroxide, aluminum phosphate or calcium phosphate), microparticles and active surface agents [such as nonionic block polymer surfactants, virosomes, saponins, meningococcal outer membrane proteins (proteosomes), immune stimulating complexes, cochleates, dimethyl dioctadecyl ammonium bromide, avridine, vitamin A or vitamin E], bacterial products [such as the cell wall skeleton of *Mycobacterium phlei*, muramyl dipeptides and tripeptides (threonyl-MDP, MDP-butyl ester, dipalmitoyl phosphatidylethalonamine MTP), monophosphoryl lipid A, *Klebsiella pneumoniae* glycoprotein, *Bordetella pertussis*, Bacillus Calmette-Guérin, V. Cholerae and *E. coli* heat-labile enterotoxin, trehalose dimycolate, CpG oligodeoxynucleotides], hormones and cytokines (for example, interleukin-2, interferon α, interferon-β, granulocyte-macrophage colony-stimulating factor, dehydroepiandrosterone, Flt3 ligand, 1,25 dihydroxyvitamin $D_3$, interleukin-1, interleukin-6, interleukin-12, human growth hormone, β-microglobulin and lymphotactin), single antigen constructs (such as multiple peptide antigens bound to a lysine nucleus or cytotoxic T-cell epitopes bound to helper T-cell epitopes and palmitoylated at the N-terminus), polyanions (such as dextrans or double-stranded polynucleotides), polyacrylics (such as polymethylmethacrylate or acrylic acid cross linked with allyl sucrose), carriers [such as tetanus toxoid, diphtheria toxoid, group B meningococcal outer membrane proteins (proteosomes), Pseudomonas exotoxins A, a cholera toxin B subunit, a heat-labile mutating enterotoxigenic *E. coli* enterotoxin, the hepatitis B virus nucleus, cholera toxin A fusion proteins, CpG dinucleotides, thermal shock proteins or fatty acids], live vectors (such as vaccinia virus, canarypox virus, adenovirus, attenuated *Salmonella typhi*, Bacillus Calmette-Guérin, *Streptococcus gordonni*, herpes simplex virus, vaccine-derived poliovirus, rhinovirus, Venezuelan equine encephalitis virus, Yersinia enterocolitica, Listeria monocytogenes, Shigella, *Bordetella pertussis* or *Saccharomyces cerevisiae*), vehicles [such as water-in-oil emulsions (for example mineral oils such as complete Freund's adjuvant or incomplete Freund's adjuvant; vegetable oils; squalene or squalane); oil-in-water emulsions, such as a mixture of squalene, Tween-80 and Span 85; liposomes; or biodegradable polymer microspheres of, for example, lactides and glycolides, polyphosphazones, betal-glucans or proteinoids], others (such as N-acetylglucosamine-3yl-acetyl-L-alanyl-D-isoglutamine, gamma insulin and aluminum hydroxide, transgenic plants, human dendritic cells, lysophosphatidylglycerol, stearyl-tyrosine or tripalmitoyl pentapeptide), or combinations thereof.

In a preferred embodiment of the second aspect of the invention, said adjuvant is aluminum hydroxide, and more preferably aluminum hydroxide gel. Therefore, a preferred embodiment of the second aspect of the invention refers to a composition, preferably a pharmaceutical composition, comprising i) a conjugate comprising at least one CysAβ(33-40) peptide (SEQ ID NO: 1) linked to the keyhole limpet hemocyanin (KLH) and ii) aluminum hydroxide gel, wherein the crosslinking agent connecting each CysAβ(33-40) peptide to the keyhole limpet hemocyanin (KLH) of the conjugate is the maleimidobutyric acid N-hydroxysuccinimide ester (SM).

It is noted that, as shown in example 5, the adsorption rates of the conjugate onto the aluminum hydroxide gel of said preferred composition depends on the pH. In fact, the adsorption rate increases at lower pH-values. A reduction from pH 7.4 to pH to 7.2 or even 7.0 does not result in significant higher adsorption rates. An adsorption at pH 6.8 shows an adsorption rate around 90%. At pH 6.0 the adsorption ratio is the highest. At a conjugate concentration based on 200 μg/mL net peptide and pH 6.7% of conjugate is still free.

Based on these analyses, in order to increase the immunogenic capacity of the pharmaceutical composition, a pH value of between 5.8 to 7.0 should be used in order to increase the adsorption rate of the conjugate onto the adjuvant and significantly increase its immunogenic capacity.

Therefore, another preferred embodiment of the second aspect of the invention refers to a composition, preferably a pharmaceutical composition, comprising i) a conjugate comprising at least one CysAβ(33-40) peptide (SEQ ID NO: 1) linked to the keyhole limpet hemocyanin (KLH) and ii) aluminum hydroxide gel, wherein the crosslinking agent connecting each CysAβ(33-40) peptide to the keyhole limpet hemocyanin (KLH) of the conjugate is the maleimidobutyric acid N-hydroxysuccinimide ester (SM), and wherein the pH of the composition ranges from 5.8 to 7.0, preferably from 6.2 to 7.0, more preferably from 5.8 to 6.2.

In further preferred embodiments of the second aspect of the invention or of any of its preferred embodiments, the concentration of CysAβ(33-40) peptides (SEQ ID NO: 1) in the pharmaceutical composition is of at least 100μg, preferably at least 150μg, more preferably from 150μg to 400μg, still more preferably from 160μg to 240μg, still more preferably about 200μg.

In yet further preferred embodiments of the second aspect of the invention or of any of its preferred embodiments, the KLH-SM-CysAβ(33-40) conjugates present in the pharmaceutical composition comprise a ratio of at least 45 CysAβ (33-40) peptides (SEQ ID NO: 1) per keyhole limpet hemocyanin (KLH) protein.

In still another preferred embodiment of the second aspect of the invention or of any of its preferred embodiments, the pharmaceutical composition in contained in glass ampoules, preferably of 1 or 1.2 ml.

It is further noted that, as reflected above, the adsorption rates of the conjugate onto the aluminum hydroxide gel of in the composition of the second aspect of the invention (when aluminum hydroxide gel is used) depends on the pH. Moreover, surprisingly the pH increases during the storage of the pharmaceutical composition once it has been manufactured thus reducing the adsorption rates if such increases reached pH values above 7.0, or preferably above 6.8. In order to diminish such drawback that clearly affects the immunogenic capacity of the pharmaceutical composition, it is important to adjust the pH of the pharmaceutical composition to a range of between 5.5 to 6.5, preferably 5.8 to 6.2, more preferably 5.9 to 6.1, at the time of manufacturing the pharmaceutical composition so that storage does not or affects minimally the immunogenic capacity of the composition.

Therefore, yet another preferred embodiment of the second aspect of the invention refers to a method to manufacture a pharmaceutical composition, which comprises the following steps:

a. Adding maleimidobutyric acid N-hydroxysuccinimide ester (SM) to a composition comprising keyhole limpet hemocyanin (KLH) in a buffer at a pH between 7.0 to 9;
b. Eliminating the excess of maleimidobutyric acid N-hydroxysuccinimide ester from the solution of step a), preferably by using 0,02 M Na-Phosphate-buffer at a pH of about 6.6 to 7.0;
c. Adding CysAβ(33-40) peptides (SEQ ID NO: 1) in DMSO to the solution of step b) at a pH of between 6.6 to 7.0 to produce the conjugates;
d. Eliminating the free peptide from step c), preferably by using 0,01 M PBS-buffer at a pH of 6,6 to 7.0;
e. Optionally filtrating the solution of step d), preferably by using a filter of about 0.2 μm.;
f. Adjusting the pH of the solution of step d) or e) to a arrange between 5.5 to 6.5, preferably 5.8 to 6.2, more preferably 5.9 to 6.1, still more preferably about 6.0; and
g. Adding aluminum hydroxide gel to the solution of step f) once the pH has been adjusted.

In a third aspect, the present invention discloses the use of a composition comprising the conjugate of the present invention for preparing a medicinal product. Preferably said composition is the composition identified in the second aspect of the invention or in any of its preferred embodiments. Also in a preferred embodiment, said medicinal product is for use in the treatment or prevention of an amyloid disease, more preferably of a amyloid disease selected from Alzheimer's disease, Parkinson's disease, cerebral amyloid angiopathy, vascular dementia of an amyloid origin, inclusion-body myositis and dementia with Lewy bodies. In the most preferred embodiment, said medicinal product is used for the prevention or treatment of Alzheimer's disease.

In a fourth aspect, the present invention relates to a method of treatment or of prevention of an amyloid disease in a patient in need of same comprising the delivery of a therapeutically effective amount of a composition comprising the conjugate of the present invention. Preferably said composition is the composition identified in the second aspect of the invention or in any of its preferred embodiments. Also in a preferred embodiment, said amyloid disease is a amyloid disease selected from Alzheimer's disease, Parkinson's disease, cerebral amyloid angiopathy, vascular dementia of an amyloid origin, inclusion-body myositis and dementia with Lewy bodies, even more preferably Alzheimer's disease.

In a final aspect, the present invention discloses a method of manufacturing antibodies characterized in that it comprises an immunization step for immunizing mammals or birds with a composition comprising the conjugate of the present invention. Preferably said composition is the composition identified in the second aspect of the invention or in any of its preferred embodiments. It is contemplated that the mammals used in such method can be ruminants, equidae, lagomorphs, primates (preferably humans) or any other mammal that allows obtaining the suitable amounts of serum for extracting or obtaining sufficient amounts of antibodies. It is contemplated that the birds used in the method of the present invention are any fowl-like birds, waterfowl, pigeons and doves or any other bird that allows obtaining suitable amounts of serum for extracting or obtaining sufficient amounts of antibodies. It is further contemplated the protection of the antibodies obtained or obtainable by the method of the final aspect of the invention as well as their use to manufacture a pharmaceutical composition for use in the treatment of an amyloid disease selected from Alzheimer's disease, Parkinson's disease, cerebral amyloid angiopathy, vascular dementia of an amyloid origin, inclusion-body myositis and dementia with Lewy bodies, even more preferably Alzheimer's disease.

Therefore, the present invention provides a conjugate generated using the crosslinking agent SM, and compositions comprising same that allow generating an greater immune response compared with conjugates generated with other crosslinking agents of the prior art.

Additionally, the immune response generated by said conjugates of the present invention or the compositions comprising said conjugates is specific for Aβ40 i.e., it allows generating anti-Aβ40 specific antibodies without generating anti-Aβ42 antibodies.

For better understanding, the present invention is described in further detail below in reference to the attached drawings presented by way of example and in reference to illustrative non-limiting examples.

Example 1. Preparation of KLH-SM-CysAβ(33-40) Conjugates

For preparing these conjugates, KLH was used as a transport protein, SM as a crosslinking agent and CysAβ (33-40) (SEQ ID NO: 1) as an immunogenic peptide (peptide with residues 33-40 of the amyloid peptide to which a cysteine has been added at the N-terminus).

Binding took place between the available lysine residues of the KLH and the cysteine added at the N-terminal end of the peptide. In this case, the binding of the crosslinking agent to KLH was done first (KLH activation step), and, in a second step, the immunogenic peptide was added to the activated KLH so that conjugation could take place.

The protocol followed for the foregoing is as follows:

A 250 mM stock solution of SM was prepared by dissolving 100 mg of SM in 680 μL of dry DMSO. Aliquots of said stock solution were made and stored at -20 °C.

KLH was dissolved at a concentration of 5 mg/mL in PBS/5mM EDTA pH 7.4.

16 μL of stock solution of SM were added for each milliliter of KLH that was conjugated.

Said solution was left to react for 2 hours and 30 minutes at room temperature under gentle stirring.

Then, the reaction buffer was changed to remove reaction byproducts and excess unreacted SM. For this purpose, a PD10 column (GE Healthcare; reference 17-0851-01) was used as follows:

Step a): The column was equilibrated with 25 mL (5 mL, 5 times) PBS (80 mM sodium hydrogenophosphate dihydrate, 20mM sodium dihydrogenophosphate monohydrate, 100mM sodium chloride) /5mM EDTA pH 7.4.

Step b): 2.5 mL of the already reacted solution were added in the column and said solution was left to penetrate, discarding the eluate.

Step c): 3.5 mL of PBS were added in the column and the eluate was collected.

Step d): The column was re-equilibrated with 25 mL (5 mL, 5 times) of 5mM EDTA pH 7.4, as explained above in step a).

Steps b) to d) were repeated all the times needed depending on the volume of solution that reacted. After that, the column was rendered equilibrated.

Step e): The column was stored at 4 °C in order to use it on other occasions with the same peptide conjugate in the same manner. Preceding protocol.

Then the peptide that was to be mixed with activated KLH was calculated. To that end, was taken into account both the molecular weight of the peptide and the molecular weight of KLH, in addition to the active sites therein (measured according to the methods known in the prior art based on measuring absorbance at 343 nm before and after treating the activated KLH solution with dithiothreitol and performing the necessary conversion). For example, for 10 mg of KLH with 1724 active sites:

10/6725000 (mean molecular weight of KLH)=$1.48\times10^{-6}$ mmol of KLH $1.48\times10^{-6}$ mmol of KLH ×1724 active sites=$2.55\times10^{-3}$ mmol of peptide required for covering all the active sites.

A 3-fold peptide excess was placed to favor the conjugation reaction:

$2.55\times10^{-3}\times3=7.65\times10^{-3}$ mmol of peptide required.

$7.65\times10^{-3}$ ×weight molecular of the peptide (834.4 Da)=mg of peptide required (6.38 mg of peptide) (applying the required conversion factors).

Once the peptide/activated KLH ratio (i.e., KLH with bound SM) was determined, the following reaction was prepared: mixture of the peptide with the activated KLH with SM in a suitable proportion. To that end, the peptide was prepared at 6 mg/mL in DMSO and was slowly added to activated KLH. The proportion of DMSO in the final reaction must not exceed 30%. If it were higher than that in any case, PBS/5mM EDTA pH 7.4 is added until the amount thereof was reduced to values of less than 30%.

The solution was left to react at room temperature and under stirring between 18 and 24 hours.

Finally, the obtained solutions were stored at 4 °C. The peptide that has not conjugated with KLH and is therefore free may or may not be removed. If said free peptide is not removed, the peptide concentration in the final product is determined by the total peptide used in the reaction, not only that which is bound to native KLH, and the final reaction volume.

Example 2. Comparison of the Immune Response of KLH-Crosslinking Agent-CisAβ(33-40) Conjugates Generated Using Different Crosslinking Agents In this case, the immune response strength generated in mice (4 per group) with the following conjugates was compared:

KLH-SM-CysAβ(33-40) (produced according to Example 1).

KLH-SPDP-CysAβ(33-40): this conjugate uses a crosslinking agent commonly used in the prior art, succinimidyl 3-(2-pyridyldithio)propionate (SPDP) and is produced by means of a protocol very similar to the one described in Example 1 (introducing the necessary adaptations) and known in the prior art.

The immune response strength test was conducted in BALB/c strain mice. The protocol that was followed was:

1. A week before the first inoculation, blood was drawn from all the mice participating in the study to obtain pre-immune serum.
2. Depending on the group to which each mouse was assigned (see Table 1 for the different analyzed groups), each mouse was inoculated the corresponding vaccine once a week for three weeks straight.
3. A week after the third shot, blood was drawn again from each of the mice participating in the study to measure the response obtained in the serum.

TABLE 1

Groups used in the study and description of the conjugate administered to each of them.

| Group | Transport protein | Crosslinking | Adjuvant |
|---|---|---|---|
| 1 | KLH, Manufacturer 1 | SM | Alhydrogel ® (aluminum hydroxide gel) |
| 2 | KLH, Manufacturer 1 | SPDP | Alhydrogel ® (aluminum hydroxide gel) |
| 3 | KLH, Manufacturer 2 | SM | Alhydrogel ® (aluminum hydroxide gel) |

TABLE 1-continued

Groups used in the study and description of the conjugate administered to each of them.

| Group | Transport protein | Crosslinking | Adjuvant |
|---|---|---|---|
| 4 | KLH, Manufacturer 2 | SM | None |
| 5 | KLH, Manufacturer 2 | SPDP | Alhydrogel ® (aluminum hydroxide gel) |
| 6 | KLH, Manufacturer 3 (GMP) | SM | Alhydrogel ® (aluminum hydroxide gel) |

The peptide dose administered to the mice in each of the groups shown in Table 1 is reflected in Table 2 included below.

TABLE 2

Peptide dose, including both total peptide and peptide conjugated to KLH administered to each of the mice in each of the groups of the study.

| Group | Total peptide dose (sum of free peptide and KLH-bound peptide) (in μg) | KLH-bound peptide dose (in μg) |
|---|---|---|
| 1 | 120 | 40 |
| 2 | 120 | 40 |
| 3 | 120 | 40 |
| 4 | 120 | 40 |
| 5 | 120 | 40 |
| 6 | 60 | 60 |

Table 3 shows a tabulated summary of the immune response strength results obtained for the different groups (analyzing serum from the mice obtained the week after finishing the therapeutic or vaccination regimen explained in the present example), together with the increase observed in the immune response (fold number the immune response increased a week after finishing the therapeutic regimen with respect to the pre-immune response). The measurement of the immune response was taken on the serum obtained from each mouse by means of indirect ELISA, according to the protocol known in the prior art, with respect to which it should be pointed out that the ELISA plates were sieved with A340 peptide. Once the corresponding steps of washing, blocking, subsequent washing, incubation with the samples to be analyzed of plasma/serum (1:3 serial dilutions starting with a 1:30 dilution) and additional washing were performed, each well was incubated with the Anti-mouse IgG (H+L) antibody HRP (the secondary antibody dilution was 1:2000 in vehicle solution at pH 8). After incubating with said antibody and washing the wells, the plate was developed by adding 100 μL per well of an ABTS solution (diammonium 2,2'-azinobis-[3-ethylbenzothiazoline-sulfonate];

Roche; reference: 102 946 001) with 0.375 mg/mL in ABTS buffer (Roche; reference: 11 112 597 001). This substrate turned green upon reacting with the peroxidase bound to the secondary antibody. The color intensity depended on the amount of antibodies bound to the plate. The reaction was incubated for 55 minutes at room temperature and in the dark, and then the absorbance was read in an ELISA plates reader at 405 nm. The obtained absorbance results were analyzed with the GraphPad Prism 3.02 program. The "One Site Competition" equation was used for the analysis:

$$Y = \text{Minimum} + \frac{(\text{Maximum} - \text{Minimum})}{1 + 10^{x - LogEC50}}$$

The $EC_{50}$ data, which is the inflection point of the curve, i.e., the point at which 50% of the maximum effect observed was produced, was obtained from the aforementioned analysis. In the present case, it was interpreted as the serum dilution at which 50% of the peptide present in the well bound to the antibody present in the serum.

TABLE 3

Mean immune response results obtained for each of the groups of the study. It includes results for the serum after the vaccine treatment (1 week after the three injections according to the protocol described in the present example) and the increase observed between said point and the pre-immune response (before starting the therapeutic regimen). The mean pre-immune $EC_{50}$ was 18.11.

| Group | Post-3 inoculation $EC_{50}$ | Increase in $EC_{50}$ (fold number) |
|---|---|---|
| 1 | 12974.95 | 716.33 |
| 2 | 580.35 | 32.04 |
| 3 | 6325.50 | 349.22 |
| 4 | 924.97 | 51.07 |
| 5 | 1.87 | 0.10 |
| 6 | 5056.00 | 279.14 |

In view of the results shown in Table 3 and the conjugate used in each of the study groups, the following can be concluded:

The different KLHs used as transport proteins (from different manufacturers), despite having a certain effect on the immune response, have not been shown to be relevant in determining the magnitude of the immune response (high immune response in groups 1, 3, 4 and 6, i.e., groups with an increase in $EC_{50}$ of 50 or more, versus a weak or inexistent immune response in groups 2 and 5, i.e., groups with an increase in $EC_{50}$ of less than 50).

The differences between obtaining a high immune response and a weak or inexistent immune response lie in the crosslinking agent used. Based on the experimental results obtained, it is deduced that the conjugates in which SM were used produce an immune response that is significantly greater that the one observed for the conjugates in which SPDP was used. In fact, the groups treated with conjugates with the crosslinking agent SM allow generating a high immune response whereas the groups treated with conjugates in which SPDP was used showed an immune response that was much weaker or inexistent.

In addition to the foregoing, the results obtained for group 4 must be highlighted, as they clearly show that the response of the conjugates generated using SM is still greater than the one observed for the conjugates generated using SPDP, even without the use of an adjuvant.

The foregoing shows that the use of SM as a crosslinking agent for preparing the KLH-crosslinking agent-CysAβ(33-40) conjugates provides vaccines with an immune response that is surprisingly greater whether said conjugate is used with an adjuvant or without an adjuvant.

Example 3. Comparison of the Degree of Conjugation (Peptide Binding to KLH) of KLH-Crosslinking Agent-CysAβ(33-40) Conjugates Generated Using Different Crosslinking Agents.

As in the case of Example 2, the conjugates for which the degree of conjugation or number of peptides bound per molecule of transport protein (KLH) was compared are:

KLH-SM-CysAβ(33-40) (produced according to Example 1).

KLH-SPDP-CysAβ(33-40) (produced as indicated in Example 2).

Table 4 shows a tabulated summary of the experimental results obtained for the experiment for binding the peptide to the transport protein that was carried out.

TABLE 4

Description of the analyzed conjugates and of the number of peptide molecules bound to each KLH molecule observed by mass spectrometry. With respect to said bonds, the table indicates one or two values depending on if one or two batches of the corresponding conjugate were analyzed.

| Transport protein | Crosslinking agent | Number of peptide molecules bound to each KLH molecule |
|---|---|---|
| KLH, Manufacturer 1 | SM | 81 |
| KLH, Manufacturer 1 | SPDP | 35/33 |
| KLH, Manufacturer 2 | SM | 70/68 |
| KLH, Manufacturer 2 | SPDP | 44/31 |

As seen in Table 4, those KLHs from different manufacturers had no effect on in the bonds result obtained. In contrast, the crosslinking agent did indeed have an enormous effect on the results obtained given that SM allowed obtaining twice the number of bonds or more, i.e., by using SM as a crosslinking agent twice the number of peptide molecules binds for each KLH molecule. This result is surprising and unexpected given that the peptide used incorporates a cysteine at the N-terminus for reacting with the crosslinking agents. According to the prior art, the incorporation of said cysteine should allow the peptide conjugation to be efficient and equivalent to any of the crosslinking agents known in the prior art. However, it was observed in this case that SM allows a more efficient conjugation reaction than SPDP does.

These binding results allowed explaining part of the results shown in Example 2 (i.e., part of the improvement observed in immune response induction and subsequent antibody generation). Nevertheless, said immune response results are not completely assimilable to the obtained binding results, which is also surprising in view of said obtained results and suggesting that the crosslinking agent contributes to increasing the immune response not only by mediating greater binding of the peptide to the transport protein.

Example 4. Immune Response Assays in Rabbits and Specificity of the Antibodies Generated.

A potency assay of vaccines comprising the KLH-SM-CysAβ(33-40) conjugates was conducted in rabbits. In this case, the rabbits were vaccinated with 200 μg of total bound peptide, said 200 μg being bound to the transport protein (chosen dose depending on preliminary studies). Each rabbit was inoculated with 1 mL of the vaccine with the previously specified dose, using 2% Alhydrogel® (aluminum hydroxide gel) as an adjuvant.

The animals were treated with the previously indicated dose by means of subcutaneous injection of the vaccine once a week for 3 straight weeks drawing blood a week before commencing the vaccination protocol and a week after finishing it.

The titration of the generated antibodies and the analysis of their specificity was done by means of ELISA, according to the protocol known in the prior art and briefly indicated in Example 2, with the following differences:

The ELISA plates were sieved with Aβ40 or Aβ42 peptide (included as SEQ ID NO: 3), depending on if specific antibodies are to be detected or those that bind to Aβ40 or to Aβ42, respectively.

The antibody used to detect the presence of antibodies in the analyzed sera was Anti-Rabbit IgG (H+L) HRP (Invitrogen; reference: 65-6120) (the secondary antibody dilution was 1:2000 in vehicle solution at pH 8).

The development reagents were those indicated in Example 2, and therefore the plates were also read at 405 nm and the same equation was applied to the results. The $EC_{50}$ data, which is the inflection point of the curve, i.e., the point at which 50% of the maximum effect observed was produced, was obtained from the analysis. As indicated in Example 2, said result was interpreted as the serum dilution at which 50% of the peptide present in the well bound to the antibody present in the serum.

According to the aforementioned titration protocol, all the samples obtained were titrated to detect Aβ40 and Aβ42 peptide antibodies. The obtained results are shown in tabulated form in Tables 5 and 6.

TABLE 5

Amount of anti-Aβ40 specific antibodies in rabbits before and after the vaccination protocol. A column relating to the increase observed as a consequence of treatment is also included.

| Identification of Rabbit | Pre-immune $EC_{50}$ | Post-3 inoculation $EC_{50}$ | Increase in $EC_{50}$ (fold number) |
|---|---|---|---|
| 71 | 36.17 | 47406 | 1310.64 |
| 72 | 7.483 | 4021 | 537.35 |
| 73 | 14.07 | 73421 | 5218.27 |
| 74 | 4.482 | 12467 | 2781.57 |
| 75 | 45.48 | 5173 | 113.74 |
| 76 | 20.5 | 98381 | 4799.07 |

TABLE 6

Amount of Aβ42 specific antibodies in rabbits before and after the vaccination protocol. A column relating to the increase observed as a consequence of treatment is also included.

| Identification of Rabbit | Pre-immune $EC_{50}$ | Post-3 inoculation $EC_{50}$ | Increase in $EC_{50}$ (fold number) |
|---|---|---|---|
| 71 | 53.88 | 0.049 | 0.00 |
| 72 | 29.24 | 0.069 | 0.00 |
| 73 | 22.49 | 2.761 | 0.12 |
| 74 | 24.05 | 15.49 | 0.64 |
| 75 | 73.18 | 0.063 | 0.00 |
| 76 | 23.37 | 34.04 | 1.46 |

Based on what is shown in Tables 5 and 6, it is deduced that the conjugate of the present invention (KLH-SM-CysAβ(33-40)) allows not only obtaining a high immune response in rabbits but also said response is specific for Aβ40 (without a significant humoral response to Aβ42), i.e., anti-Aβ40 specific antibodies are generated in the immune response that do not bind to Aμ42.

The results included in Examples 1 to 4 prove and confirm the technical advantages and effects explained above in the description, proving that the use of SM as a crosslinking agent allows generating KLH-crosslinking agent-CysAβ (33-40) conjugates that generate a greater immune response with respect to when another crosslinking agent of the prior art is used. Additionally, KLH-SM-CisAβ(33-40) conjugates allow generating high immune responses in mice and rabbits, specific for Aβ40 (without a significant humoral response to Aβ42), i.e., anti-Aβ40 specific antibodies that do not bind to Aβ42 are generated in said immune responses. Said examples validate the usefulness of the conjugate of the present invention in the treatment of amyloid diseases, preferably Alzheimer's disease, in mammals, preferably in humans.

Example 5. Adsorption Studies for KLH-SM-CysAβ(33-40) Conjugates Onto the Aluminum Hydroxide Gel.

1.35 mg/ml, peptide is equivalent to 14.4 mg/ml conjugate KLH-SM-CysAβ(33-40).

TABLE 7

| μg/mL based on peptide net | μg/mL peptide net supernatant | equivalent to Abeta-X40-KLH supernatant [mg/mL] | % conjugate free in solution | % adsorbed |
|---|---|---|---|---|
| 100 | 12 | 0.128 | 12 | 88 |
| 125 | 15 | 0.160 | 12 | 88 |
| 150 | 19 | 0.203 | 13 | 87 |
| 175 | 25 | 0.267 | 14 | 86 |
| 200 | 35 | 0.373 | 18 | 83 |

Study 2: Adsorption-dependency of pH at defined concentrations

Testing 1
220 μg peptide

| pH | μg/mL peptide net supernatant | equivalent to Abeta-X40-KLH supernatant [mg/mL] | % conjugate free in solution | % adsorbed |
|---|---|---|---|---|
| 7.4 | 38 | 0.41 | 17 | 83 |
| 7.2 | 37 | 0.39 | 17 | 83 |
| 7.0 | 33 | 0.35 | 15 | 85 |
| 6.8 | 25 | 0.27 | 11 | 89 |
| 6.5 | 21 | 0.22 | 10 | 90 |
| 6.0 | 15 | 0.16 | 7 | 93 |

Testing 2
150 μg peptide

| pH | μg/mL peptide net supernatant | equivalent to Abeta-X40-KLH supernatant [mg/mL] | % conjugate free in solution | % adsorbed |
|---|---|---|---|---|
| 7.4 | 18 | 0.19 | 12 | 88 |
| 7.2 | 18 | 0.19 | 12 | 88 |
| 7.0 | 15 | 0.16 | 10 | 90 |

-continued

Testing 2
150 μg peptide

| pH | μg/mL peptide net supernatant | equivalent to Abeta-X40-KLH supernatant [mg/mL] | % conjugate free in solution | % adsorbed |
|---|---|---|---|---|
| 6.8 | 10 | 0.11 | 7 | 93 |
| 6.5 | 11 | 0.12 | 7 | 93 |
| 6.0 | 0 | 0.00 | 0 | 100 |

Testing 3
200 μg peptide

| pH | μg/mL peptide net supernatant | equivalent to Abeta-X40-KLH supernatant [mg/mL] | % conjugate free in solution | % adsorbed |
|---|---|---|---|---|
| 7.4 | 13 | 0.14 | 13 | 87 |
| 7.2 | 13 | 0.14 | 13 | 87 |
| 7.0 | 12 | 0.13 | 12 | 88 |
| 6.8 | 9 | 0.10 | 9 | 91 |
| 6.5 | 0 | 0.00 | 0 | 100 |
| 6.0 | 0 | 0.00 | 0 | 100 |

In these studies the influence of the concentration of conjugate on the adsorption rate as well as the influence of the pH on the adsorption rate were determined. In the first experiment the adsorption rate of different concentrations of conjugate in a defined amount of aluminium hydroxide (0.35% corresponds to the permitted dose of 1.25 mg Al per single dose) and the defined pH 7.4 (physiological pH) was tested. At the physiological testing conditions (pH 7.4) 12 to 18% free conjugate was detected in the supernatant. A reduction of the amount of peptide to 100 μg peptide does not yield higher adsorption rates.

In a second study the influence of the pH on the adsorption rate was determined. The pH was altered (pH 6.0 to pH 7.4) at defined conjugate concentrations (based on 100 μg, 150 μg and 220 pg peptide net/mL). As illustrated in the results shown above, the adsorption rate depends on the pH. In fact, the adsorption rate increases at lower pH-values (see tables): A reduction from pH 7.4 to pH to 7.2 or even 7.0 does not result in significant higher adsorption rates. An adsorption at pH 6.8 shows an adsorption rate around 90%. At pH 6.0 the adsorption ratio is the highest. At a conjugate concentration based on 200 μg/mL net peptide and pH 6, 7% of conjugate is still free.

Based on these analyses, in order to increase the immunogenic capacity of the pharmaceutical composition of the invention, a pH value of between 5.8 to 7.0 should preferably be used in order to increase the adsorption rate of the conjugate onto the adjuvant.

Although the invention has been described with respect to preferred embodiments, the latter must not be considered to be limiting of the invention, which will be defined by the broadest interpretation of the following claims.

What is claimed is:

1. A composition comprising aluminum hydroxide gel and a conjugate of at least one CysAβ(33-40) peptide (SEQ ID NO: 1) linked to the keyhole limpet hemocyanin (KLH), wherein the crosslinking agent connecting each CysAβ(33-40) peptide to the keyhole limpet hemocyanin (KLH) of the conjugate is the maleimidobutyric acid Nhydroxysuccinimide ester (SM), wherein at least 45 CysAβ(33-40) peptides (SEQ ID NO: 1) is linked to each keyhole limpet hemocyanin (KLH).

2. A pharmaceutical composition comprising i) a conjugate comprising at least one CysAβ(33-40) peptide (SEQ ID NO: 1) linked to keyhole limpet hemocyanin (KLH) via a crosslinking agent, and ii) an aluminum hydroxide gel, wherein the crosslinking agent connecting each CysAβ(33-40) peptide to the keyhole limpet hemocyanin (KLH) of the conjugate is maleimidobutyric acid N-hydroxysuccinimide ester (SM), and wherein a pH of the composition ranges from 5.8 to 7.0.

3. The pharmaceutical composition according to claim 2, wherein the pH of the composition ranges from 6.2 to 7.0.

4. The pharmaceutical composition according to claim 2, wherein the pH of the composition ranges from 5.8 to 6.2.

5. The pharmaceutical composition according to claim 2, wherein the concentration of the at least one CysAβ(33-40) peptide (SEQ ID NO: 1) is at least 100μg.

6. The pharmaceutical composition according to claim 2, wherein the concentration of the at least one CysAβ(33-40) peptide (SEQ ID NO: 1) is at least 150μg.

7. The pharmaceutical composition according to claim 2, wherein the concentration of the at least one CysAβ(33-40) peptide (SEQ ID NO: 1) is from 150μg to 400μg.

8. The pharmaceutical composition according to claim 2, wherein the concentration of the at least one CysAβ(33-40) peptide (SEQ ID NO: 1) is from 160μg to 240μg.

9. A glass ampule comprising the pharmaceutical composition of claim 2.

* * * * *